SUGAR CANE
Filed May 24, 1963 3 Sheets-Sheet 1
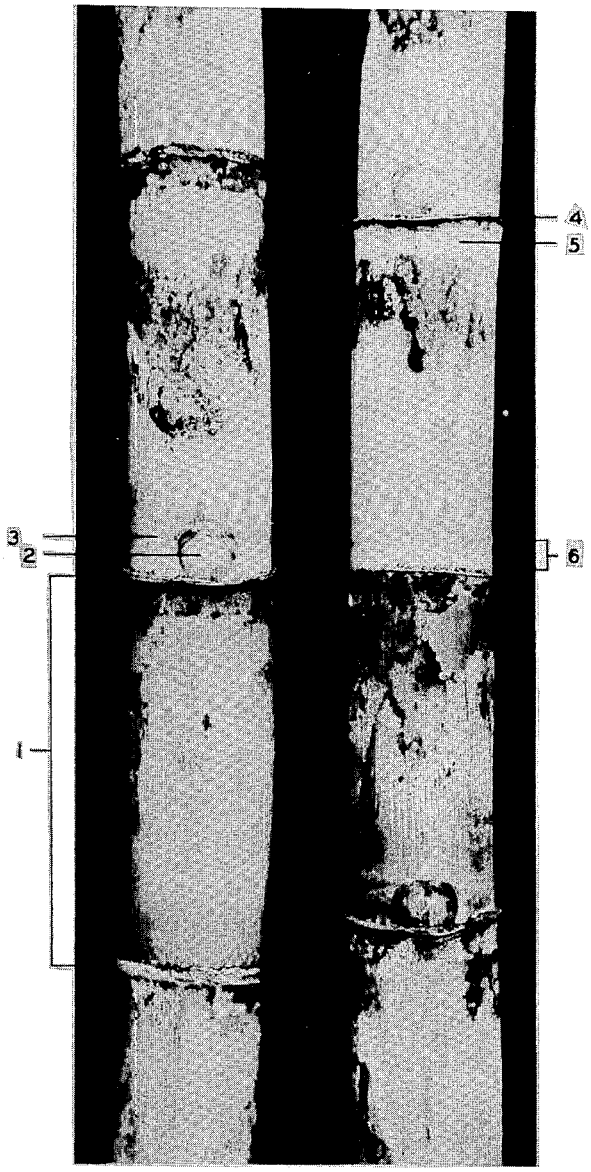
Fig. I.
INVENTORS
LESLIE M. WEETMAN
BENJAMIN A. BOURNE
BY Cushman, Darby & Cushman
ATTORNEYS SUGAR CANE
Filed May 24, 1963 3 Sheets-Sheet 2
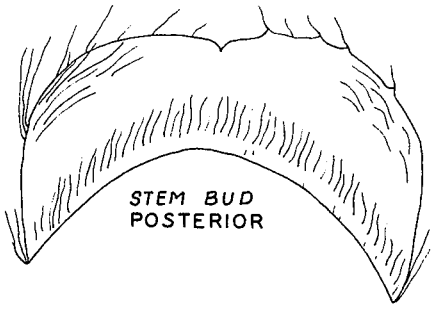
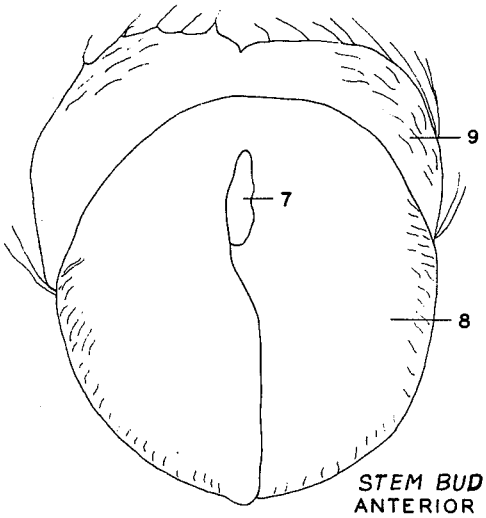
FIG. II
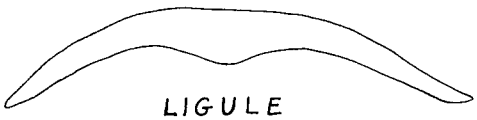
LIGULE
FIG. IV
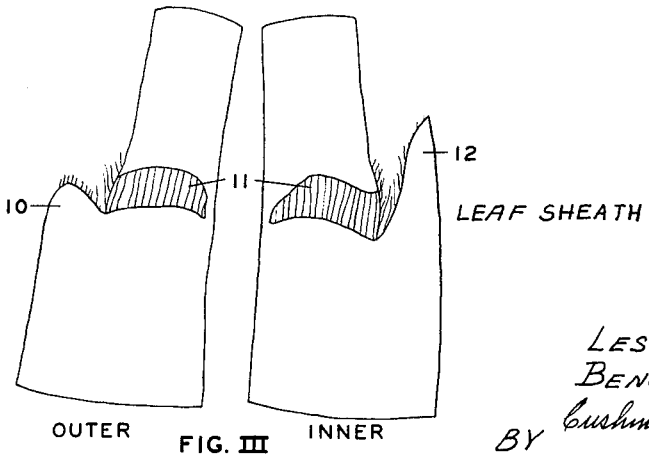
FIG. III
INVENTORS
LESLIE M. WEETMAN
BENJAMIN A. BOURNE
BY Cushman, Darby & Cushman
ATTORNEYS SUGAR CANE
Filed May 24, 1963 3 Sheets-Sheet 3
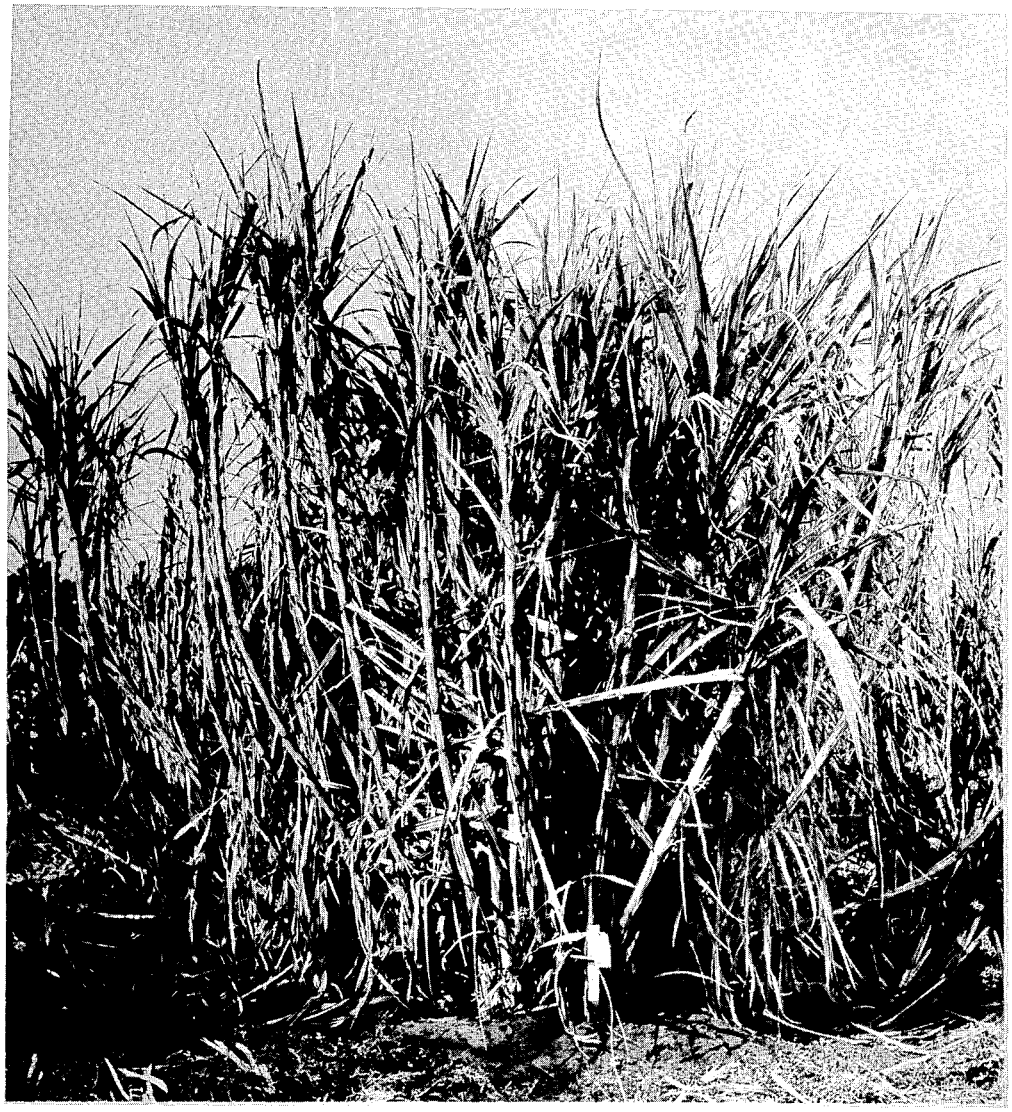
FIG. V
INVENTORS
LESLIE M. WEETMAN
BENJAMIN A. BOURNE
BY Cushman, Darby & Cushman
ATTORNEYS United States Patent Office Plant Pat. 2,510
Patented May 11, 1965

2,510
SUGAR CANE

Leslie M. Weetman and Benjamin A. Bourne, Clewiston, Fla., assignors to United States Sugar Corporation, Clewiston, Fla., a corporation of Delaware Filed May 24, 1963, Ser. No. 283,113
1 Claim. (Cl. Plt.—89)

This new variety of sugar cane originated as a seedling produced by the inventors by crossing the variety Cl. 49–54 as female and the variety Cl. 47–83 as male. (In this form of variety designation, which is well known to sugar cane breeders, "Cl": denotes the breeding locality or station, i.e, Clewiston, Florida; "47" represents the year that the particular variety was first grown, i.e. 1947; and "83" is the distinctive number assigned to that variety among those grown in that year.) The cross was made in December 1953, at Clewiston, Florida, and this new variety was selected from among the progeny of this cross. The inventors have subsequently propagated the variety at Clewiston, Florida, by means of stem cuttings under the identifying number Cl. 54–334.

In replicated variety trials extending over five crop years, juice analyses were made in early November and again in January or February each year. Average indicated yields of 96° sugar per ton of cane were 239 pounds for the November analyses and 245 pounds for the January-February analyses. These data indicate very early maturity and high sucrose content over a long possible harvest period. This variety is also vigorous and produces a high tonnage of cane per acre.

A series of comparative field tests with this variety, replicated five times, to study the effect of heat treatment at 50° C. for 24 hours in order to eliminate the ratoon stunting virus, has shown that even when 100% infected, there was no significant reduction in the yield of either cane or sugar per acre when harvested toward the middle of the usual cane grinding season, or in January. If harvested early in the season, however, such as November 15th, the heat-treated, ratoon stunting disease-free cane was found to yield significantly less sugar per ton of cane, amounting to 14.8 lbs. Therefore, no heat treatment for this disease is recommended, since the variety is very resistant thereto and such treatment would only have detrimental effects on the earliness of maturity.

Repeated tests have been conducted to determine the resistance of this variety to the four strains of mosaic disease virus, namely "A," "B," "D" and "E" recorded in Florida. In one test alone, 36 plants of the new variety were inoculated with a potent mixture of all four mosaic strains, such potency being shown by the fact that 100% infection of the susceptible control variety C.P. 31–294 was obtained, using 16 control plants tested under identical conditions. Not a single case of mosaic infection has ever occurred in the new variety in any of these artificial inoculation experiments. Further, a 40-foot row planting of the variety has been exposed for more than a year under field conditions providing for natural insect transmission of all four strains of the mosaic virus existing in sugar cane plants established in close proximity to the new variety and no infected plants have resulted. Therefore, the new variety has been found immune to all four strains of mosaic virus recorded in Florida when exposed to both artificial and natural means of virus transmission.

From a milling standpoint, the expressed juice of the new variety has been studied in regard to its mineral constituents such as phosphates and calcium, since these are important factors affecting juice clarification and evaporator scaling. These tests showed that the phosphate level was approximately the same as that normally occurring in the other commercial varieties. The calcium content of the juice was also found to be at a level similar to that of the regular commercial varieties grown in the Florida Everglades which are usually fairly high. Therefore, the evaporator scaling problem should be no greater than that now being experienced commercially.

In the drawings:

FIGURE I is a photographic view of approximate midsections of typical stalks, showing internode 1, stem bud 2, growth ring 3, leaf scar 4, wax ring 5 and root band 6;

FIGURE II shows anterior and posterior views of the stem bud, showing germ pore 7, prophyll 8 and wing 9;

FIGURE III is a view of the two separated and flattened halves of the upper part of a leaf sheath, showing the outer auricle 10, the inner auricle 12 and the dewlap or blade joint 11;

FIGURE IV is a view showing the outline of a ligule after its removal from the inner surface of the leaf sheath; and FIGURE V is a photographic view showing the normally erect habit of growth of the mature cane.

DETAILED DESCRIPTION

In the following detailed description of the new variety of sugar cane the terminology used in morphological description and numbering of hair groups is that employed by Artschwager. (See Sugarcane (*Saccharum officinarum* L.): Origin, Classification, Characteristics, and Description of Representative Clones by Ernst Artschwager and E. W. Brandes. Agriculture Handbook No. 122. United States Department of Agriculture, 1958.) Color descriptions are made by referring to the plates of Maerz and Paul. (See A Dictionary of Color, second edition, by A. Maerz and M. Rea Paul. McGraw-Hill Book Company, 1950.)

*The stalk (or culm)*

*Habit of growth* (see FIGURE V).—Mature stalks are usually erect but they may lean. The internodes are usually straightly aligned.

*Size.*—The stalks are usually 8 to 10 feet or more in length, averaging 113 inches. They are slightly elliptical in cross-section, averaging 29.9 x 32.6 millimeters in the middle part of the stalk. The larger diameter may vary from 27 to 38 millimeters.

*Flesh.*—The color of the flesh is approximately Maerz and Paul's designation 11–H-2 and is rather uniform throughout the cross-section of the stalk. The flesh is quite solid. Fiber content is medium, averaging 11% of the weight of the stalk.

*Internodes* (1, FIGURE I).—They are cylindrical to slightly concave-convex in shape and are 9 to 15 centimeters long in the middles of the stalks, averaging 11.3 centimeters. There are usually no bud furrows. Corky cracks or growth cracks are not evident.

*Color.*—On portions of the stalk still protected by leaf sheaths, the basic color just above the growth ring is approximately Maerz and Paul's 10–E–2 to 10–F–2 (straw—color). Higher up on each internode a fairly heavy wax coating causes a whitish appearance which is in turn splotched with gray or black because of mold growth. The wax coating merges into a heavy wax ring (5, FIGURE I). Portions of the stalk exposed to direct sunlight may turn red. However, old leaves and sheaths remain attached to the stalks so that very few are exposed. Freshly stripped stalks give a general impression of light yellow and gray, with many parts covered by black mold.

*Growth ring* (3, FIGURE I).—It is about 1.5 to 2 millimeters tall in the middle of the stalk and only slightly tumescent. The color approximates Maerz and Paul's designation 12–G–6 to 12–H–6.

*Root band* (6, FIGURE I).—The shape is cylindrical to slightly obconoidal. The height is 8 to 10 millimeters on the bud side and 6 to 8 millimeters on the opposite side. The color is slightly lighter than the basic color of the internode. There are three rows of root primordia.

*Leaf scar* (4, FIGURE I).—The leaf scar protrudes and is usually slightly oblique and slightly depressed under the buds.

*Epidermal cells.*—The pattern of the stem epidermis is predominantly Artschawger's type 2 in which single short cork cells alternate with long epidermal cells in a regular pattern. However, about 18% of the cork cells have a single silica cell associated to make a group of two short cells. Also, in about 6% of cases, there are two cork cells instead of one. Most of the short cells have rectangular ends, but occasionally they are pointed. There is an average of 657 short cell groups per square millimeter. The long cells average 12.1 microns in width. Stomata are present, the number averaging 3.6 per square millimeter.

*Stem buds*

*General characteristics.*—The buds (2, FIGURE I) are inserted at or slightly below the edge of the leaf scar. The tips extend to, and sometimes exceed, the growth ring. The buds are not protruding nor overly prominent and have an average size of about 11.8 millimeters wide by 11.0 millimeters tall. The color approaches that of the internodes. The prophyll (8, FIGURE II) is round with radial venation and has a near-central germ pore (7, FIGURE II).

*Wings of the prophyll* (9, FIGURE II).—The wings are inserted above the middle of the prophyll and are fairly broad with broad tips.

*Pubescence.*—Hairs are most prominent on the wings and lower margins of the prophyll. They may be dense and long, or they may be sparse. The most prominent hair groups appear to be 1, 4, 13, 26, 14 and 18, but each of these is highly variable. Most of the hairs are appressed and heavily coated with wax.

*The leaf*

*The blade.*—The habit of the blade is ascending with drooping tip. The color is dark green. The larger leaves on each stalk are 6 to 7.5 centimeters wide, averaging 6.8, and are 127 to 155 centimeters long, averaging 143. The ratio of the length of the blade to the width thereof averages 21.

*The sheath.*—The sheaths have an average length of 31 centimeters. Group 57 hairs occur sparsely over a linear area 10–15 centimeters long and 2 to 5 millimeters wide. These hairs are closely appressed and are not spinelike. Groups 56 and 60 are apparently absent. The older sheaths adhere to the stalks to full maturity of the cane.

*Dewlaps* (11, FIGURE III).—The dewlaps are somewhat variable in color, but often approach Maerz and Paul's 13–J–2, which is darker than the green of the leaf. The shape is double-crescent. The outer surface of the dewlap is covered with fine short hairs (Group 58) near the margin, but is nearly or quite glabrous toward the midrib. Some longer hairs of Groups 58*a* are usually present near the margin. This outer surface is overlaid with a heavy coating of wax. The inner surface is covered with moderately dense short hairs which extend across the midrib. Longer hairs of Group 51 are often present near the margin.

*Auricles.*—The outer auricle (10, FIGURE III) is usually ascending transitional in shape and averages about 4 millimeters in length. The inner auricle (12, FIGURE III) is usually lanceolate in shape and varies from 7 to 35 millimeters in length, being most often between 10 and 20 millimeters.

*Ligules* (FIGURE IV).—The ligule is broadly crescent shaped with broad lozenge. It measures 37 to 42 millimeters in length and 4 to 5 millimeters tall. The dorsal surface is covered with long, closely adnate hairs. The marginal cilia (Group 61) are only ¼ to ⅓ millimeter in length and are irregular in length giving a "fringed" appearance under magnification.

*Inflorescence.*—Under Florida conditions, this variety usually blooms in December, although in some seasons it may not flower at all, and it is male-sterile.

Important characteristics which, in combination, help to distinguish this new variety of sugar cane from all other known varieties are:

(1) Very early maturity.

(2) High sucrose content over a long possible harvest period.

(3) High resistance or immunity to strains "A," "B," "D" and "E" of sugar cane mosaic virus, both by natural and artificial means of transmission in south Florida.

(4) High resistance to or tolerance of the ratoon stunting disease, making heat treatments unnecessary.

(5) Stalks which remain generally erect at maturity.

(6) Stalks slightly elliptical in cross-section with diameters in the middle parts of the stalks averaging 29.9 x 32.6 millimeters.

(7) Medium fiber content of stalks.

(8) Bud furrows usually absent.

(9) Growth ring short, averaging 1½ to 2 millimeters tall.

(10) Three rows of root primordia on the root band.

(11) A stem epidermal pattern which is predominantly like Artschwager's type 2 in which single short cork cells alternate with long epidermal cells in a regular pattern, but with certain modifications as described.

(12) Stomata present in the stem epidermis.

(13) Prophyll of the stem bud round in shape with radial venation and a near central germ pore.

(14) Wing of prophyll with a broad tip.

(15) Wing inserted above the middle of the prophyll.

(16) Leaf sheaths adhering closely to the stalks until full maturity of the cane.

(17) Hairs on the leaf sheath covering only a narrow area and not spine like.

(18) Dewlaps variably double-crescent in shape.

(19) Hairs extending across the midrib on the inner surface of the dewlap.

(20) Outer auricles usually ascending transitional in shape.

(21) Inner auricles usually lanceolate and varying from 7 to 35 millimeters in length.

(22) ligule broadly crescent-shaped with broad lozenge.

(23) Marginal cilia of ligule uneven in length and measuring only ¼ to ⅓ millimeter.

(24) Flowers male-sterile in Florida.

What is claimed is:

The new and distinct variety of sugar cane herein shown and described, identified by the combination of the characteristics enumerated above.

No references cited.

ABRAHAM G. STONE, *Primary Examiner.*